(12) United States Patent
Yuen

(10) Patent No.: US 8,121,664 B2
(45) Date of Patent: Feb. 21, 2012

(54) SENSOR

(75) Inventor: Paul Anthony Yuen, Hong Kong (CN)

(73) Assignee: Dayton Technologies Limited, Central, Hong Kong Sar (CN)

( * ) Notice: Subject to any disclaimer, the term of this patent is extended or adjusted under 35 U.S.C. 154(b) by 748 days.

(21) Appl. No.: 12/195,281

(22) Filed: Aug. 20, 2008

(65) Prior Publication Data
US 2010/0004524 A1    Jan. 7, 2010

(30) Foreign Application Priority Data
Jul. 4, 2008    (HK) .................................. 08107402.9

(51) Int. Cl.
*A61B 5/0408*    (2006.01)
(52) U.S. Cl. .......................... 600/390; 600/391; 600/509
(58) Field of Classification Search .................. 600/372, 600/382–392, 395–397
See application file for complete search history.

(56) References Cited

U.S. PATENT DOCUMENTS

| | | | | |
|---|---|---|---|---|
| 3,474,775 A | * | 10/1969 | Johnson | 600/397 |
| 3,954,100 A | * | 5/1976 | Sem-Jacobsen | 600/393 |
| 4,300,575 A | * | 11/1981 | Wilson | 607/152 |
| 4,478,225 A | * | 10/1984 | Ewing | 600/519 |
| 4,515,162 A | * | 5/1985 | Yamamoto et al. | 600/391 |
| 4,706,680 A | * | 11/1987 | Keusch et al. | 600/392 |
| 4,729,377 A | * | 3/1988 | Granek et al. | 600/393 |
| 5,337,748 A | * | 8/1994 | McAdams et al. | 600/396 |
| 5,817,012 A | * | 10/1998 | Schoendorfer | 600/362 |
| 5,974,344 A | * | 10/1999 | Shoemaker, II | 607/149 |
| 6,577,897 B1 | * | 6/2003 | Shurubura et al. | 600/547 |
| 2003/0097165 A1 | * | 5/2003 | Krulevitch et al. | 607/115 |
| 2007/0088227 A1 | * | 4/2007 | Nishimura | 600/509 |
| 2007/0285868 A1 | | 12/2007 | Lindberg et al. | |
| 2009/0076362 A1 | * | 3/2009 | Jaatinen | 600/372 |

* cited by examiner

*Primary Examiner* — Lee Cohen
*Assistant Examiner* — Erin M. Cardinal
(74) *Attorney, Agent, or Firm* — Buchanan Ingersoll & Rooney PC

(57) ABSTRACT

A sensor for sensing physiological signal from outside the human body, said sensor comprising an electrode for abutment against the skin; and a transmission conductor electrically connected to said electrode, said transmission conductor formed from a flexible material, wherein in use a substrate is disposed between the skin and said transmission conductor, and said substrate is permeable to moisture and air thereby exposing said transmission conductor to said moisture.

30 Claims, 4 Drawing Sheets

From Inside

Side Sectional view A-A

Bottom View (Sensor Only, No Substrate etc)

SENSOR

TECHNICAL FIELD

This invention relates to a sensor for measuring a physiological signal from the skin. In particular the invention is described with reference to a sensor that can be used with a heart rate meter.

BACKGROUND

Conventional heart-rate belts and heart rate bands typically comprise a body made of plastic, on the surface of which there are two local electrodes to be placed against the chest. Electronics for transmitting a heart rate signal, typically to a wrist-band device, are built into the plastic body. Conductors from the electrodes to the electronics also run inside the body, which is generally attached against the chest with the aid of a flexible band.

Because plastic heart rate bands are relatively thick and can feel uncomfortable in use, heart rate belts and sensors utilizing textile materials have recently been developed. However some of these developments have the disadvantage of unreliable contacts, electrical insulation, and interference of electrical signals. These disadvantages with the prior art are discussed in US Patent Application Publication No. 2007/0285868 (Lindberg et al).

The sensor arrangement disclosed in US Patent Application Publication No. 2007/0285868 overcomes some of the problems with the prior art by ensuring that the transmission conductor that interconnects the electrode with the electronics module is well insulated. In this prior art the sensor is made from a number of layers, two of which are insulation layers. One of these insulation layers has the task of preventing liquid, for example perspiration from reaching the transmission conductor layer and thereby preventing electrical interference. However, this sensor arrangement of multiple layers is laborious and costly to make.

The object of the present invention is to provide a sensor that overcomes or substantially ameliorates at least one of the problems associated with the prior art.

SUMMARY OF THE INVENTION

According to a first aspect the present invention consists in a sensor for sensing physiological signal from outside the human body, said sensor comprising an electrode for abutment against the skin, a transmission conductor electrically connected to said electrode, said transmission conductor formed from a flexible material, and wherein in use a substrate is disposed between the skin and said transmission conductor, and said substrate is permeable to moisture and air thereby exposing said transmission conductor to said moisture.

Preferably said moisture increases conductivity with minimal interference to the electrical connection between said transmission conductor and said electrode.

Preferably said flexible material is a substantially plastic material including carbon black.

Preferably said substantially plastic material is a rubberized material.

Preferably said electrode and transmission conductor consist of a single piece formed from essentially the same material.

Preferably said transmission conductor is electrically connected to an electrical contact zone that allows for said sensor to be connected to an electronics module.

Preferably said electrical contact zone is a metallic conductor.

Preferably said electronics module contains means for transmitting, recording or displaying a physiological signal.

Preferably said sensor of the first aspect can be used in a heart rate belt.

Preferably said substrate is a flexible textile material.

Preferably an adhesive layer is disposed between said substrate and said transmission conductor, and said adhesive layer is perforated to allow moisture and air to permeate between said substrate and said transmission conductor.

Preferably said substrate is an innermost layer of a belt or apparel.

Preferably in embodiment at least a portion of said transmissive conductor is permeable to moisture and air.

Preferably said portion is porous.

Preferably said portion has a plurality of apertures therein.

According to a second aspect the present invention consists in a sensor for sensing physiological signal from outside the human body, said sensor comprising an electrode for abutment against the skin, and a transmission conductor that electrically connects said electrode to an electronics module, said electrode and said transmission conductor consist of a single piece of substantially plastic material, wherein in use at least one flexible substrate that is permeable to moisture and air is disposed between the skin and said transmission conductor thereby exposing said transmission conductor to body moisture, said moisture increasing conductivity with minimal interference to the electrical connection between said electrode and said electronic module.

Preferably said substantially plastic material includes carbon black.

Preferably said substantially plastic material is a rubberized material.

Preferably said flexible substrate is an innermost layer of a belt or apparel.

According to a third aspect the present invention consists in a sensor for sensing physiological signal from outside the human body, said sensor comprising a single piece of substantially plastic material having at least an electrode portion for abutment against the skin, and at least a transmission conductor portion that electrically connects said electrode portion to an electronics module, wherein in use said sensor is held against the skin by a means of attachment having at least one flexible layer that is permeable to moisture and air, said at least one flexible layer is disposed between said transmission conductor portion and said skin, such that said transmission conductor portion is exposed to moisture, and wherein said moisture increases conductivity with minimal interference to the electrical connection between said electrode portion and said electronic module.

Preferably said substantially plastic material includes carbon black.

Preferably said substantially plastic material is a rubberized material.

Preferably said means of attachment is a belt or apparel.

According to a fourth aspect the present invention consists in a sensor for sensing physiological signal from outside the human body, said sensor comprising an electrode for abutment against the skin, a transmission conductor electrically connected to said electrode, and wherein the transmission conductor and a substrate disposed between the skin and transmission conductor are permeable to moisture and air, and said moisture increases conductivity with minimal interference to the electrical connection between said transmission conductor and said electrode.

Preferably said electrode and said transmission conductor consist of a single piece of substantially plastic material including carbon black.

In a third aspect, the present invention consists in a for sensing physiological signal from outside the body of an animal, said sensor comprising an electrode for abutment against the skin; and a transmission conductor electrically connected to said electrode, said transmission conductor formed from a flexible material, wherein in use a substrate is disposed between the skin and said transmission conductor, and said substrate is permeable to moisture and air thereby exposing said transmission conductor to said moisture.

Preferably, the sensor is suitably sized and for application in conjunction with a horse, and the sensor is used for performance monitoring and training of the horse.

In a fourth aspect, the present invention consists in a system including the sensor of the third aspect, including further sensors for detection of other parameters.

Preferably, said further sensors include at least one of temperature, relative humidity, altitude, riding speed and distance sensors.

Preferably, the system further includes at least one of embedded accelerometer circuits for detection of horse running patterns and styles for characteristic classification, radar modules may be provided having high speed capturing capability for measurement of riding speed and distance of the horse during training and racing activity; and embedded radio frequency transmission means for wireless data transmission to a remote processor for activity analysis.

Preferably, the system according to the fourth aspect provides for at least analysis of horse health conditions from instant heart rate, average heart rate, maximum heart rate, resting heart rate and recovery heart rate of the horse with respect to difference conditions such as environmental temperature, relative humidity, altitude, riding speed and distance; estimation of maximum riding speed and optimised racing distance of the horse by monitoring heart rate conditions and recovery heart rate against different riding manners, speeds and distances; rider and/or trainer classification of characteristics of the horse for pursuing optimum riding manner and method for the horse by analyzing the performances in relation to different riding speeds, speeds, distances, manners and methods.

DESCRIPTION OF PREFERRED EMBODIMENTS

Figure 1:
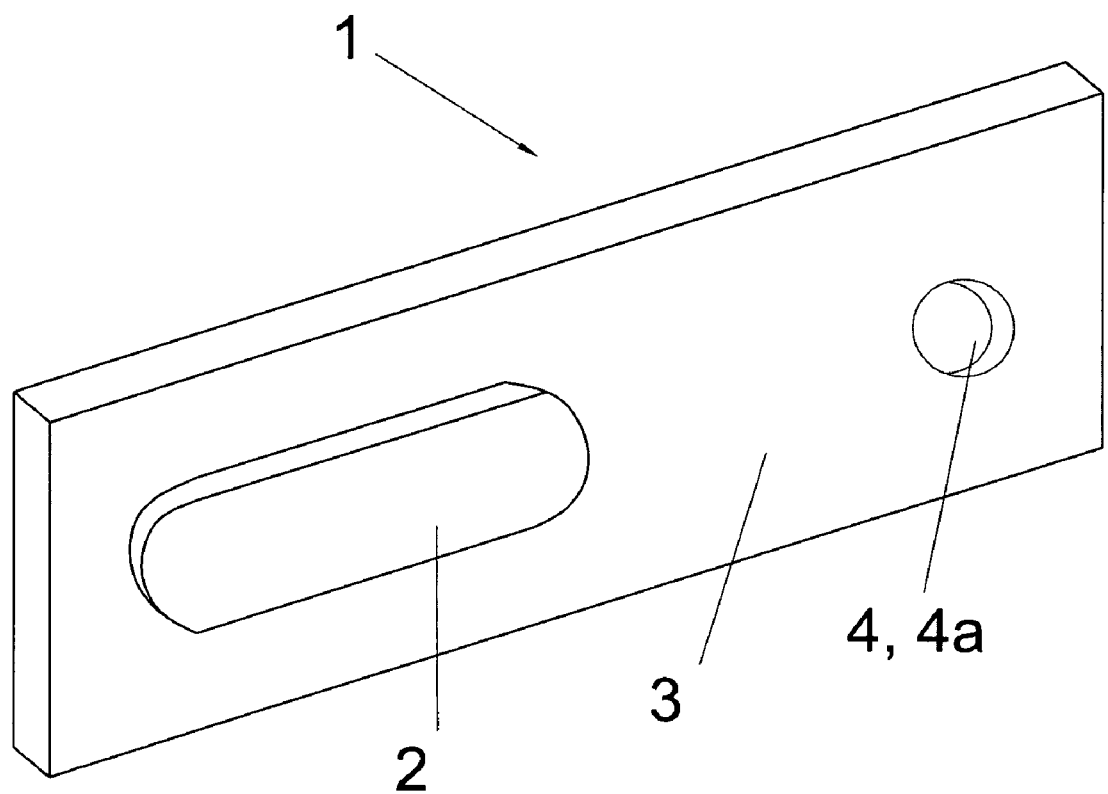
FIG. 1 depicts a perspective view of a first embodiment of a sensor in accordance with the present invention.

Referring to the drawings, a sensor 1 in accordance with the present invention is described with reference to FIGS. 1 to 5, and is used to detect heart rate. Sensor 1 comprises an electrode 2 and a transmission conductor 3.

Sensor 1 is preferably made of a substantially flexible plastic or polymeric material, and more preferably is a rubberized material that includes "carbon black" to provide electrical conductivity.

Those skilled in the art will appreciate that other materials may utilised having applicable structural and electrical properties in other or alternate embodiments, whilst falling Preferably in its simplest form, electrode 2 and a transmission conductor 3 of sensor 1 are integrally formed from the same material. In a preferred embodiment, sensor 1 is about 2 to 3 mm thick, about 20 to 30 mm wide and about 120 to 180 mm in length.

A metallic terminal 4 attached to transmission conductor 3 is used to provide an "electrical contact zone" so that sensor 1 may be connected to an electronics module 5. Terminal 4 may be riveted to transmission conductor 3, and have a plastic insulation cap 4a on its underside as shown in FIG. 5.

Figure 2:
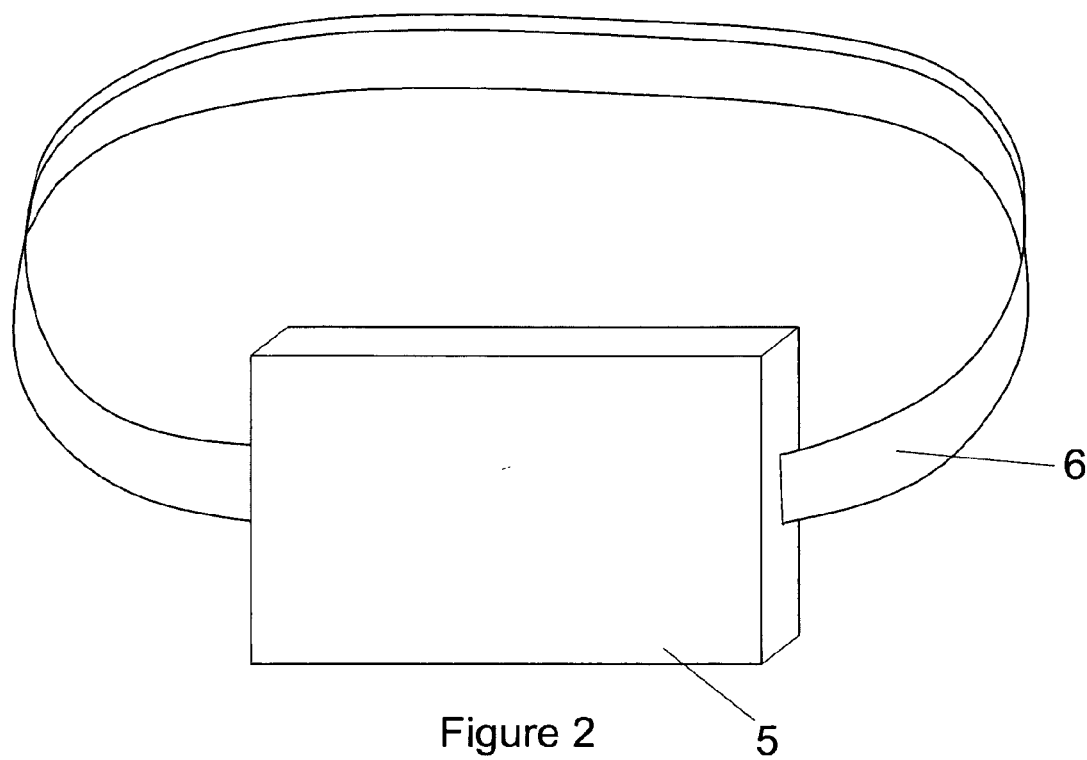
FIG. 2 depicts a heart rate belt with an electronics module that utilizes two of the sensors shown in FIG. 1.
Figure 3:
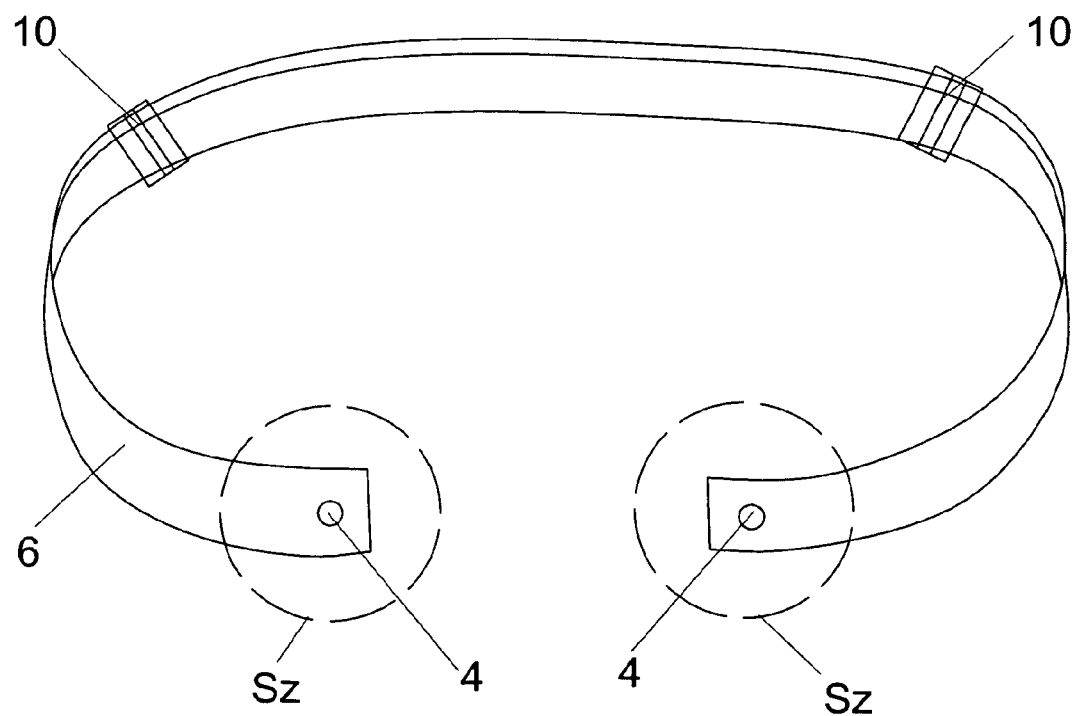
FIG. 3 depicts heart rate belt of FIG. 2 with the electronics module removed to display the zones at which sensors are located, and their respective terminals to which the electronics module is attached.

Sensor 1 and electronics module 5 are supported by an adjustable belt 6 intended to be worn around a user's chest, as shown in FIGS. 2 and 3. Belt 6 would typically have two identical sensors 1, each attached to electronics module 5. The location of the two sensors within belt 6 is best shown in FIG. 4 by sensor zones Sz and the respective terminals 4.

Belt 6 may for example be a stretchable textile band, incorporating adjustment devices 10 for adjustment for a user's girth. Sensor 1 is housed within belt 6, which has a flexible and stretchable substrate layer 7 that abuts against the skin when the belt is worn by a user.

Figure 4:
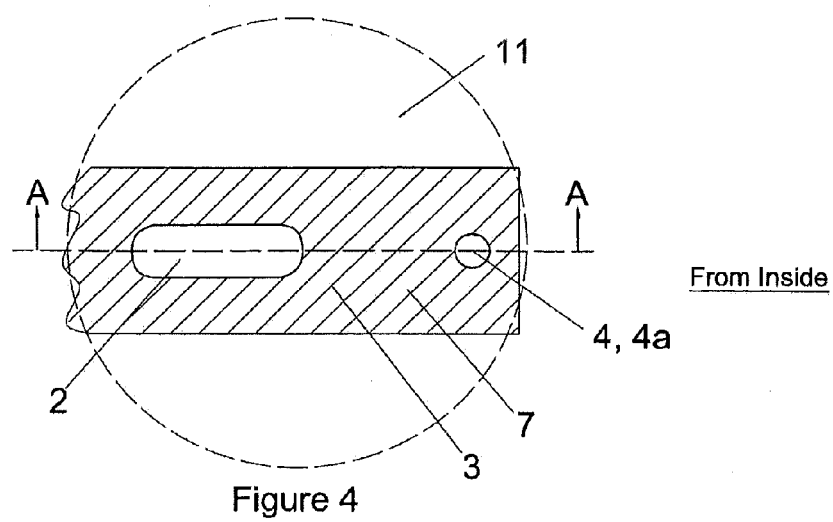
FIG. 4 depicts an inner (contact) side view of the belt of FIG. 2, at a zone where the sensor is located.
Figure 5:
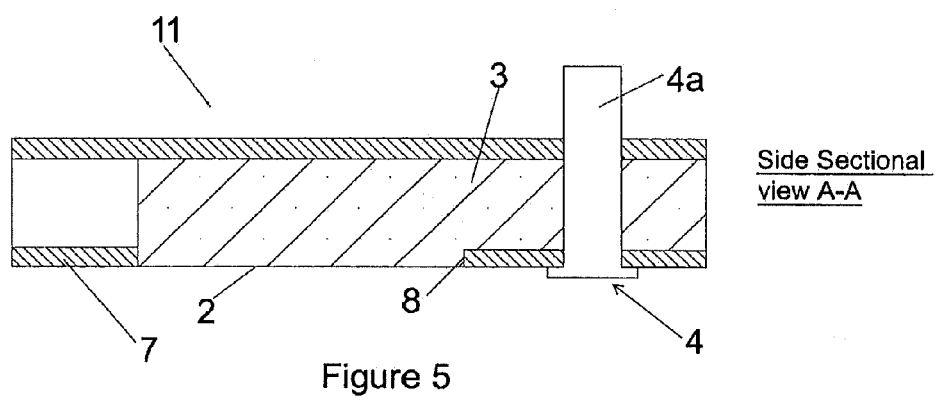
FIG. 5 depicts a side-sectional view of the sensor through lines A-A of FIG. 2, and the surrounding flexible substrate that is part of the belt.

For ease of reference this embodiment is now described in relation to one of these sensors 1, with reference to FIGS. 4 and 5. FIG. 4 depicts the contact or "electrode-side" of the sensor 1, which in use is placed against the skin of a user. Electrode 2 protrudes though an aperture 8 in substrate layer 7 of the belt 6, so that in use it is able to abut against the skin of a user. A portion of substrate layer 7 is disposed between transmission conductor 3 and the skin, adjacent to electrode 2.

Preferably the substrate layer 7 is a textile material that is permeable to moisture and air. Sensor 1 may preferably be held in place on the belt by a glue adhesive between substrate layer 7 and transmission conductor 3. The glue adhesive is preferably perforated so that moisture and air is able to pass therethrough.

In use, when belt 6 is worn around a user's chest, electrode 2 of sensor 1 is abutted against the skin. The substrate layer 7 of belt 6 is exposed to body moisture and air, and as it is a permeable textile material, body moisture and air can permeate through substrate 7 and the perforations in the glue adhesive, so that moisture comes in contact with transmission conductor 3.

This moisture and air coming in to contact with transmission conductor 3 has been found to improve the electrical connection and conductivity without causing interference between electrode 2 and electronics module 5 attached to terminal 4, thereby providing improved acquisition and transmission of a heart rate signal.

In this embodiment the exposure of the transmission conductor 3 to moisture is beneficial to acquisition and transmission of a heart rate signal. This is markedly different to the prior art US Patent Application Publication No. 2007/0285868 (Lindberg et al), which insulates the transmission conductor from the skin's moisture in a water-tight manner.

Whilst the abovementioned embodiment is described with reference to a sensor 1 that may be used with a belt 6 for the purposes of a heart rate meter, it should be understood that the sensor 1 may be abutted against a user's chest by some other means of attachment. For example, the sensor 1 may be attached to apparel worn by the user, and the inner flexible substrate layer 7 shown in the abovementioned embodiment, may for example be an innermost layer of the apparel.

Whilst the abovementioned embodiment is described with respect to sensor 1 being used to detect and transmit a heart rate signal, it should be noted that the sensor of the present invention may be used to detect and transmit some other physiological signal, such as the contraction of a user's muscle somewhere else in the body. In such an embodiment the sensor would be attached to some other part of the user's body such as an arm or a leg, and may be of different dimensions to that of the abovementioned embodiment.

It should be understood that whilst the abovementioned embodiment describes two sensors 1 being used in a heart rate belt 6, there may be applications for detecting a physiological signal where only a single sensor 1 is required.

Figure 6:
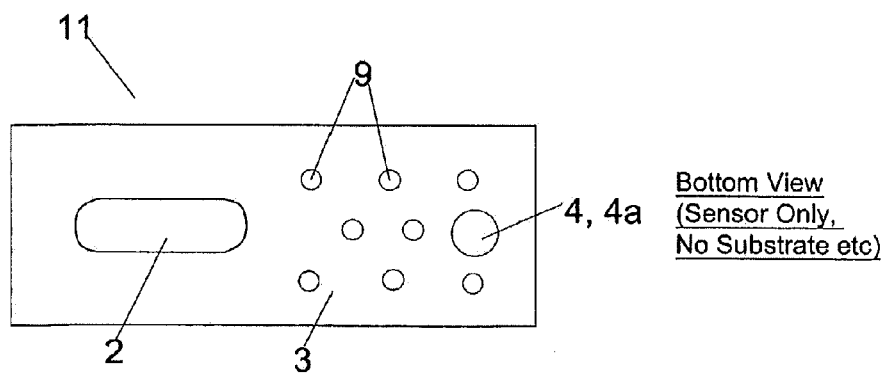
FIG. 6 depicts a contact side view of a second embodiment of a sensor in accordance with the present invention.
Figure 7:
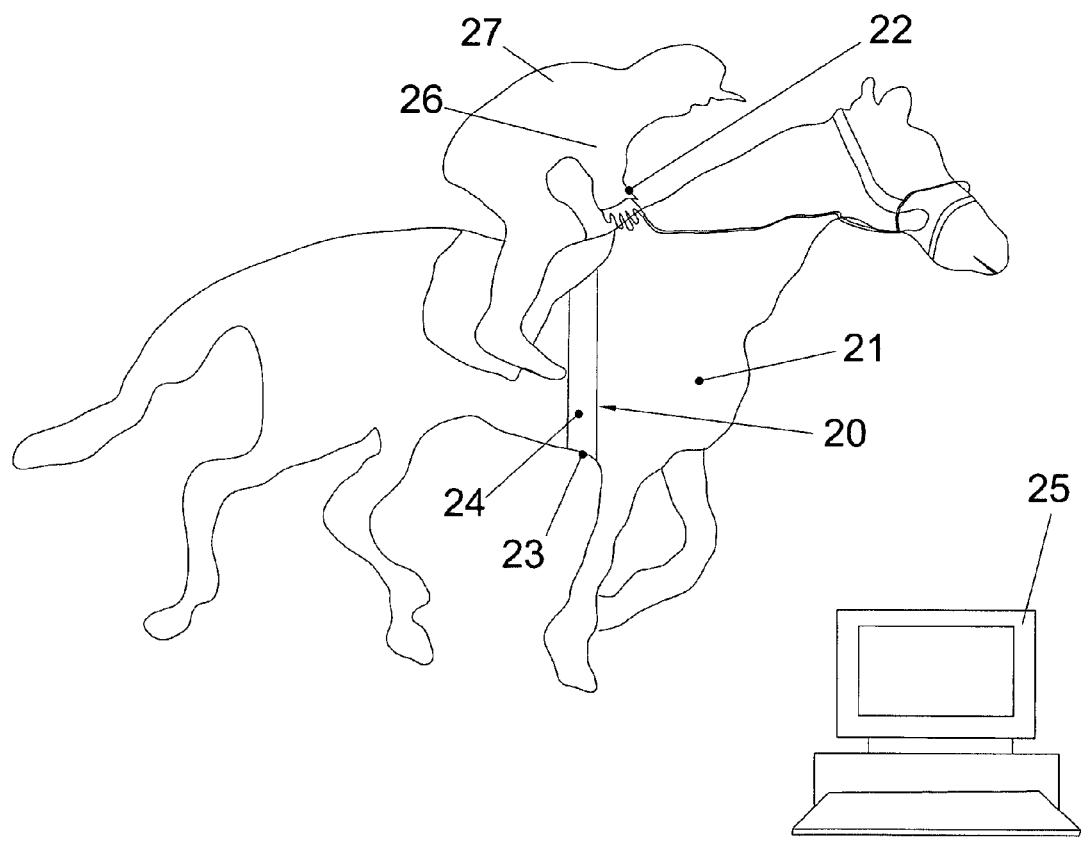
FIG. 7 depicts a third embodiment of a sensor in accordance with the present invention.

In a second embodiment, a sensor 11 having an electrode 2 and a transmission conductor 3 similar to sensor 1 of the first embodiment is shown in FIG. 6. However, in this embodiment the transmission conductor 3 is optionally provided with holes 9 that allow moisture and air to pass there through. By allowing air to pass through the conductor, enhanced user comfort is provided, allowing the body to breathe through the transmission conductor. As will be understood, by having a porous transmission conductor, the transmission conductor may be broader without causing discomfort to the user, thus having a more efficient transmission conductor.

In other embodiments, it will be understood such a sensor 11 according to the present invention may be used without the need for a flexible substrate to be disposed between the skin and transmission conductor 3.

In a third embodiment, a sensor 20 is provided which has sufficient length so as to be adapted for use with a horse 21, for monitoring of physiological signals.

In this embodiment, the sensor may be used for training of horses, based upon performance indicators. In such an implementation, the heart rate may be monitored, and in conjunction with other sensing means for monitoring parameters such as riding speed, running distance and altitude, the data obtained from such sensors may be utilised for monitoring health and performance of the horse, and also for training purposes.

The embodiment as described may be implemented within a system for performance monitoring, wherein the following features may be provided
(i) analysis of horse health conditions from instant heart rate, average heart rate, maximum heart rate, resting heart rate and recovery heart rate of the horse with respect to difference conditions such as environmental temperature, relative humidity, altitude, riding speed and distance;
(ii) estimation of maximum riding speed and optimised racing distance of the horse by monitoring heart rate conditions and recovery heart rate against different riding manners, speeds and distances;
(iii) rider 27 and trainer can classify the characteristics of the horse and achieve optimum riding manner and method for the horse by analyzing the performances in relation to different riding speeds, speeds, distances, manners and methods;
(iv) embedded accelerometer circuits 22 may be provided for detection of horse running patterns and styles for characteristic classification;
(v) radar modules 23 may be provided having high speed capturing capability which may be utilised for measurement of riding speed and distance of the horse during training and racing activity; and
(vi) embedded radio frequency transmission means 24 may be provided for wireless data transmission to a remote processor 25 or local processor 26 for activity analysis.

Advantages of the transmission conductor of the sensor according to the present invention which is exposed to moisture include increased electrical efficiency, which increases conductivity and heart rate signal detection, an advantage over the above described prior art.

An advantage of having an integrally formed electrode and transmission conductor of a preferred embodiment, in addition to increased electrical efficiency, which provides for ease of manufacture, the structural integrity and strength characteristics of the device are increased, thus allowing the provision of a more robust and durable sensor.

Still further, by providing a sensor as herein described with reference to the invention, without an intermediate or insulation layer, allows ease of implementation within a physiological signal detecting device such as a heart rate monitoring belt. This also reduces manufacturing costs and simplicity.

The terms "comprising" and "including" (and their grammatical variations) as used herein are used in inclusive sense and not in the exclusive sense of "consisting only of".

The invention claimed is:

1. A sensor for sensing physiological signals from outside a human body, said sensor being adapted to be held against a skin of a user during use and comprising:
an electrode for abutment against the skin; and
a transmission conductor on which there is disposed a flexible substrate, wherein said flexible substrate is moisture permeable and said electrode protrudes through said flexible substrate and said electrode and said transmission conductor are integrally formed from a flexible conductive material and being adapted for wearing on a body of the user, and wherein in use the moisture permeable substrate is disposed between the skin and said transmission conductor and abuts against the skin, thereby exposing said transmission conductor to said moisture and facilitating signal acquisition from said skin.

2. A sensor as claimed in claim 1, wherein said moisture increases conductivity between said transmission conductor and said skin with minimal interference to the electrical connection between said transmission conductor and said electrode during use, thereby facilitating signal acquisition by the transmission conductor from said skin.

3. A sensor as claimed in claim 1, wherein said flexible material is a substantially plastic material including carbon black.

4. A sensor as claimed in claim 3, wherein said substantially plastic material is a rubberized material.

5. A sensor as claimed in claim 1, wherein said sensor has a thickness of about 2-3 mm, a width of about 20-30 mm, and a length of about 120-180 mm.

6. A sensor as claimed in claim 1, in which said transmission conductor is riveted to a terminal that allows for said sensor to be connected to an electronics module.

7. A sensor according to claim 6, further comprising said electronics module, and said electronics module contains means for transmitting, recording or displaying a physiological signal.

8. A sensor as claimed in claim 1, wherein said moisture permeable substrate is a stretchable textile material.

9. A sensor as claimed in claim 1, wherein said flexible substrate is a flexible textile material.

10. A sensor as claimed in claim 1, wherein said sensor comprises an adhesive layer which is disposed between said flexible substrate and said transmission conductor, said adhesive layer being perforated to allow moisture and air to permeate between said flexible substrate and said transmission conductor.

11. A heart rate monitoring belt which comprises at least one sensor as claimed in claim 1.

12. A heart rate monitoring belt which comprises a sensor as claimed in claim 1, and wherein an innermost layer of said belt includes said flexible substrate.

13. An apparel which comprises a sensor as claimed in claim 1, and wherein an innermost layer of said apparel includes said flexible substrate.

14. A sensor as claimed in claim 1, wherein at least a portion of said transmission conductor is permeable to moisture and air.

15. A sensor as claimed in claim 14, wherein said portion is porous.

16. A sensor as claimed in claim 14, wherein said portion has a plurality of apertures therein.

17. A sensor belt adapted to be worn around a user's chest for sensing physiological signals from outside a human body, said sensor belt comprising:
a sensor which is held on an adjustable belt, said sensor including,
an electrode for abutment against the skin,
a transmission conductor that electrically connects said electrode to an electronics module, said electrode and said transmission conductor formed of a single piece of substantially plastic material, and a moisture permeable flexible substrate layer wherein said electrode protrudes through the moisture permeable flexible substrate layer, wherein the moisture permeable flexible substrate layer is disposed on said transmission conductor such that in use said transmission conductor abuts against the skin and is exposed to body moisture, thereby facilitating signal acquisition from the user.

18. A sensor belt as claimed in claim 17, wherein said substantially plastic material includes carbon black, and the flexible substrate layer is a textile material.

19. A sensor belt as claimed in claim 17, wherein said substantially plastic material is a rubberized material, and said flexible substrate layer is stretchable.

20. A heart rate belt which comprises a sensor belt as claimed in claim 17, wherein the moisture permeable flexible substrate layer forms part of said sensor belt.

21. An apparel which comprises a sensor belt as claimed in claim 17, and wherein an innermost layer of said apparel includes said flexible substrate layer.

22. A sensor for sensing physiological signals from outside a human body, said sensor comprising:
a single piece of substantially plastic material having at least an electrode portion for abutment against the skin, and at least a transmission conductor portion that electrically connects said electrode portion to an electronics module, wherein in use said electrode portion and said transmission of said sensor is held against the skin by a means of attachment having at least one flexible layer that is permeable to moisture and air, said at least one flexible layer is disposed between said transmission conductor portion and said skin, such that said transmission conductor portion is exposed to moisture and said electrode protrudes through said flexible layer, and wherein said moisture increases conductivity between said transmission conductor and said skin to facilitate signal acquisition by said transmission conductor from said skin with minimal interference to the electrical connection between said electrode portion and said electronics module.

23. A sensor as claimed in claim 22, wherein said substantially plastic material includes carbon black.

24. A sensor as claimed in claim 23, wherein said substantially plastic material is a rubberized material.

25. A sensor as claimed in claim 23, further comprising said means of attachment, wherein said means of attachment is a belt or apparel.

26. A sensor for sensing physiological signals from outside a human body, said sensor comprising:
an electrode for abutment against a skin of a user;
a transmission conductor electrically connected to said electrode;
a flexible substrate disposed on said transmission conductor, wherein said electrode and said flexible substrate are adapted to be held against the skin of the user during use, and said electrode protrudes from said flexible substrate, and wherein both the transmission conductor and the flexible substrate are permeable to moisture and air, and wherein said transmission conductor and said flexible substrate are adapted such that, during use, body moisture of the user increases conductivity between said transmission conductor and said skin to facilitate signal acquisition by said transmission conductor from said skin with minimal interference to the electrical connection between said transmission conductor and said electrode.

27. A sensor as claimed in claim 26, wherein said electrode and said transmission conductor consist of a single piece of substantially plastic material including carbon black.

28. A sensor belt, comprising:
an adjustable belt adapted to be worn around a user's chest; and
a sensor according to claim 26, wherein the flexible substrate is an integral part of the adjustable belt.

29. A sensor for sensing physiological signals from outside the body of an animal, said sensor being adapted to be held against a skin of a user during use comprising:
an electrode for abutment against the skin; and
a transmission conductor on which there is disposed a flexible substrate, wherein said flexible substrate is moisture permeable and said electrode protrudes through said flexible substrate wherein said transmission conductor is electrically connected to said electrode, and said electrode and said transmission conductor are integrally formed from a flexible conductive material and adapted for wearing on a body of the user; and wherein in use the moisture permeable substrate is disposed between the skin and said transmission conductor and abuts against the skin, thereby exposing said transmission conductor to said moisture and facilitating signal acquisition from said skin.

30. A sensor according to claim 29, wherein the sensor is adapted for performance monitoring and training of horses.

* * * * *